United States Patent [19]

Nambudiry et al.

[11] Patent Number: 5,152,983

[45] Date of Patent: Oct. 6, 1992

[54] SUNSCREEN COMPOSITIONS COMPRISING PONGOMOL

[75] Inventors: Mayara E. N. Nambudiry; Visweswaria N. Collur, both of Bombay, India

[73] Assignee: Chesebrough-Pond's USA Co., Division of Conopco, Inc., Greenwich, Conn.

[21] Appl. No.: 612,041

[22] Filed: Nov. 9, 1990

[30] Foreign Application Priority Data

Nov. 10, 1989 [GB] United Kingdom ............ 8925473

[51] Int. Cl.$^5$ .............................................. A61K 7/44
[52] U.S. Cl. ..................................... 424/60; 549/469; 424/59; 514/469
[58] Field of Search ............. 549/469, 434, 435, 436; 424/60, 59; 514/469

[56] References Cited

U.S. PATENT DOCUMENTS

| | | | |
|---|---|---|---|
| 3,275,520 | 9/1966 | Strobel et al. | 424/60 |
| 3,448,190 | 6/1969 | Baron et al. | 424/59 |
| 4,426,380 | 1/1984 | Wenk et al. | 424/244 |
| 4,489,057 | 12/1984 | Welters et al. | 424/47 |
| 4,656,029 | 4/1987 | Grollier et al. | 424/47 |
| 4,814,162 | 3/1989 | Lang et al. | 424/47 |
| 4,988,501 | 1/1991 | Gosciniak | 424/59 |

FOREIGN PATENT DOCUMENTS

| | | |
|---|---|---|
| 0020274 | 12/1980 | European Pat. Off. . |
| 0238302 | 9/1987 | European Pat. Off. . |
| 2285853 | 9/1975 | France . |
| 1473483 | 5/1977 | United Kingdom . |
| 2073018 | 10/1981 | United Kingdom . |

OTHER PUBLICATIONS

Rao et al, CA 70(22) 101380z, "Preparation and absorption . . . " etc. Curr. Sci. 1969 38(5), 110.
Bader et al, Cosmetics & Toiletries (1981), 96 (10) pp. 67-74.
Fox, Cosmetics & Toiletries (1987), 102 (3), pp. 41-65.
Patent Abstracts of Japan, vo. 11, No. 163 (C-424) (2610) (Shiseido Co.) (1985).

*Primary Examiner*—Richard L. Raymond
*Assistant Examiner*—B. Bembenick
*Attorney, Agent, or Firm*—Milton L. Honig

[57] ABSTRACT

A sunscreen composition suitable for topical application to human skin or hair, to provide protection from excessive exposure to ultra-violet rays, comprises:
i) an effective amount of a substituted 1,3-diketone having an ultra-violet absorption band within the range of from 250 to 500 nm, and an extinction coefficient E of from 5,000 to 70,000; and
ii) a physiologically acceptable vehicle for the substituted 1,3-diketone.

3 Claims, No Drawings

SUNSCREEN COMPOSITIONS COMPRISING PONGOMOL

FIELD OF THE INVENTION

The invention relates to compositions comprising natural plant product isolates useful as sunscreen compounds for topical application to human skin and hair to provide enhanced protection from the damaging effects of sunlight.

BACKGROUND AND PRIOR ART

The damaging effects of sunlight on human skin have been observed since time immemorial and many remedies have been proposed to protect the skin from this damage.

In general terms, harmful ultra-violet (UV) rays, particularly those originating from sunlight, which penetrate the upper atmosphere and reach the earth's surface, can be classified into:

i. the energy-rich UV-B rays (290-320nm wavelength) which possess an intense physiopathological activity on the skin; these are absorbed just above the dermis and they are responsible for erythema and skin pigmentation, and ii. UV-A rays (320-400nm wavelength) which penetrate deeper into the skin (to the dermis and beyond). Their energy is much lower and the photobiological effects they cause are much more long term in nature, for example, they accelerate skin ageing.

Certain synthetic organic substances (sunscreens) whose molecules absorb the harmful ultra-violet rays have been proposed for use in mitigating the deleterious effects of ultra-violet radiation. Examples include:

2-hydroxy-4-methoxy-4-methyl benzophenone also known as Benzophenone 10 (CTFA), and available from Ward Blenkinsop under the Trade Name UVISTAT 2211;

2-hydroxy-4-n-octyloxybenzophenone, also known as Benzophenone 12 (CTFA), and available from American Cyanamid under the Trade Name CYASORB UV 531;

2,2',4,4'-tetraheptoxybenzophenone, also known as Benzophenone 2 (CTFA), and available from BASF Chemical Co. under the Trade Name UVINUL D50;

4-t-butyl-4'-methoxydibenzoylmethane, also known as Butyl Methoxy Dibenzoyl Methane (CTFA), and available from Givaudan Coporation under the Trade Name PARSOL 1789; and 2-ethylhexyl-p-methoxy cinnamate, also known as Octyl Methoxycinnamate (CTFA), and available from Givaudan Corporation under the Trade Name PARSOL MCX.

Some of these substances absorb more effectively in UV-A range thereby providing filtering of UV radiation in this range, while others are more effective in the UV-B range.

A common problem exists, however, whatever the choice of synthetic organic sunscreen, for protection from whichever wavelength of ultra-violet radiation, and this is that physiological damage to the body can occur, following topical application of these sunscreens in quantities necessary to provide effective filtering of harmful ultra-violet radiation. Even those synthetic organic sunscreens that are believed to be safe to use in this way, necessarily have safety limits imposed, based on the quantity applied to the skin, which can result in only moderate to poor protection from harmful ultra-violet radiation.

Natural hydroxy anthracenic polyglycosides have been reported as sunscreens (Bader et al, Cosmetics & Toiletries (1981), 96 (10) 67) and the use of coffee oil as a sunscreen has been reported in French Patent 2 479 688. Similarly, extracts of jujube fruits (JP 84-227813) and aloe extract (U.S. Pat. No. 4,656,029) are stated to be useful in skin applications.

Natural extracts of aloe, frangula, senna and cascara containing anthraquinone derivatives have also been reported as useful sunscreen agents (Fox, Cosmetics & Toiletries (1987), 102 (3), 41).

These prior observations suggesting use of the natural materials as sunscreen agents have generated only limited commercial use, and none is as effective as most of the aforementioned synthetic sunscreens.

We have now discovered a series of substituted 1,3-diketones, which can be isolated from natural sources, which have wide spectrum absorption properties spanning both the UV-A & UV-B ranges, and which can be employed as sunscreen agents in cosmetic compositions particularly suited for topical application to the skin or hair. These naturally occurring substituted 1,3-diketones can accordingly be used in place of synthetic UV-A & UV-B screening compounds in skin compositions, such as those, particularly PARSOL 1789, referred to hereinbefore.

DEFINITION OF THE INVENTION

Accordingly, the invention provides a composition suitable for topical application to human skin or hair to provide protection from excessive exposure to ultra-violet rays, which comprises an effective amount of a substituted 1,3-diketone, having an ultra-violet absorption band in the range of from 250 to 500 nm, and an extinction coefficient $\epsilon$ of from 5,000 to 70,000, together with a physiologically acceptable vehicle for the substituted 1,3-diketone.

DISCLOSURE OF THE INVENTION

The substituted 1,3-diketone

The composition according to the invention comprises as a sunscreen a substituted 1,3-diketone in an amount sufficient to provide protection from excessive exposure to ultra-violet rays.

The substituted 1,3-diketone will normally have an absorption band in the region of from 250 to 500 nm, spanning both the UV-A and UV-B ranges, and an extinction coefficient $\epsilon$ of from 5,000 to 70,000.

Preferably, the sunscreen has a basic 1,3-diketone chromophore and suitable auxochrome groups providing at least one absorption band in the 280-450 nm region and an extinction coeffcient $\epsilon$ of from 10,000 to 60,000.

A preferred group of sunscreens for use in the composition according to the invention are shown by tautomeric structures (1) and (2):

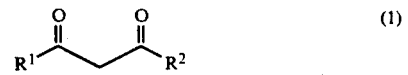

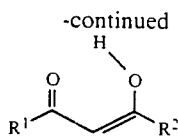
(2)

wherein R¹ and R² may be the same or different, and are chosen from benzylidine, substituted benzylidine, phenyl or substituted phenyl groups.

Preferred examples of the groups R¹ and R² are shown in the following structures (3) to (7):

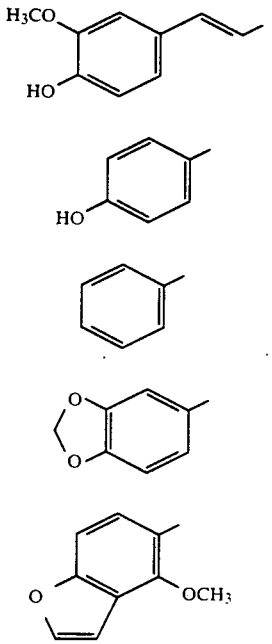

Specific examples of natural compounds for use in the composition of the invention are curcumin, and its analogues demethoxy and didemethoxy curcumin, which can be isolated from *Curcuma longa* roots, an pongamol which can be isolated from *Pongamia glabra* seeds.

Curcumin is also known as di-4-hydroxy-3-methoxycinnamoyl methane and has the structure (8):

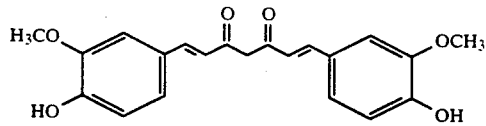

Pongamol is also known as 1,3-propanedione, 1-(4-methoxy-5-benzofuranyl)-3phenyl and has the structure (9):

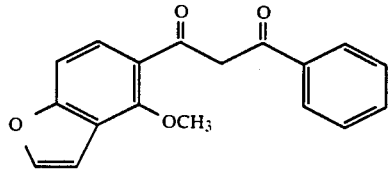

The compounds used in the compositions of the invention are effective as sunscreen agents either as pure compounds, as a concentrate of an appropriate natural isolate which comprises the substituted 1,3-diketone compound, or as a crude extract of the natural source material or even as the natural source material itself. For example, karanja oil can be used in this manner as a source of pongamol.

The composition according to the invention preferably comprises from 0.01 to 15% by weight of the substituted 1,3-diketone.

The Physiologically Acceptable Vehicle

The composition according to the invention also comprises a physiologically and cosmetically acceptable vehicle to act as a dilutant, dispersent or carrier for other materials present in the composition, so as to facilitate their distribution when the composition is applied to the skin and/or hair.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as propane, butane, isobutane, dimethyl ether, carbon dioxide, nitrous oxide;

Solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The physiologically acceptable vehicle will usually form from 10 to 99.9%, preferably from 50 to 99% by weight of the composition, and can, in the absence of other cosmetic adjuncts, form the balance of the emulsion.

OPTIONAL SKIN BENEFIT MATERIALS AND COSMETIC ADJUNCTS

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or oily material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile.

Suitable non-volatile silicones include polyalkyl siloxanes, polyalkylaryl siloxanes or mixtures thereof.

Examples of polyalkyl siloxanes include polydimethyl siloxanes having a viscosity of from 5 to 100,000 centistokes at 25° C. These siloxanes are available commercially from the General Electric Company as the Viscasil series and from Dow Corning as 244, 245, 344, 345, 200/5 and 200 fluids. Other examples include Silicones 7202 and 7518 from Union Carbide and SWS 03314 from Stauffer Chemical.

The viscosity can be measured by means of a glass capillary viscometer as set forth in Dow Corning Corporate Test Method CTM004 Jul. 20, 1970.

Also suitable is polydiethyl siloxane.

Examples of polyalkylaryl siloxanes include polymethylphenyl polysiloxanes having a viscosity of from 15 to 65 centistokes at 25° C. These siloxanes are available commercially from the General Electric Company as SF 1075 methyl phenyl fluid or from Dow Corning as 556 Cosmetic Grade Fluid.

Suitable volatile silicones are cyclic or linear polydimethyl siloxanes. The number of silicone atoms in the cyclic silicones is 3 to 7, most preferably 4 or 5. The general formula for cyclic silicones is:

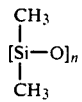

wherein n is an integer of from 3 to 7. Viscosities are generally less than 10 centipoise (cP) at 25° C.

Linear polydimethyl siloxanes are those having a viscosity of less than 5cP at 25° C. The linear volatile silicones usually contain from 3 to 9 silicon atoms and have the general formula:

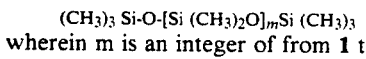

wherein m is an integer of from 1 to 7.

Silicones of the above described types are widely available and examples include those available from Dow Corning such as 244, 245, 344, 345, 200/5 and 200 Fluids from Union Carbide such as Silicone 7202 and 7158, and from Stauffer Chemical such as SWS-03314.

The oil or oily material, when present for the purposes for forming an emulsion, will normally form up to 90%, preferably from 10 to 80% by volume of the composition.

It is to be understood that the oil or oily material when present can also possess emollient properties and can accordingly also function as a physiological acceptable vehicle as hereinbefore defined.

Emulsifier

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of > 6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |

TABLE 1-continued

| Chemical Name of Emulsifier | Trade Name | HLB Value |
|---|---|---|
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 80%, preferably from 5 to 80% by volume.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

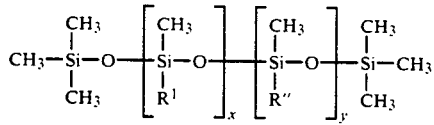

where the groups R' and R" are each chosen from —H, $C_{1-8}$ alkyl and —$[CH_2CH_2O]_a[CH_2CHO]_bH$

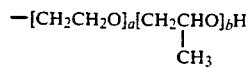

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 5 to 0.75 one of groups R' and R" being lauryl, and the other having a molcular weight of from 1000 to 5000.

A particularly preferred dimethyl polysiloxane polymer is one in which:
a has the value 14
b has the value 13
x has the value 249
y has the value 1.25

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Optional Organic sunscreens

The composition of the invention optionally can comprise a synthetic organic sunscreen, in addition to the substituted 1,3-diketone obtainable from natural plant sources, as hereinbefore defined, further to enhance the benefit of the composition in providing protection from the harmful effects of excessive exposure to sunlight.

As has already been stated, some synthetic organic sunscreens can be harmful to health if applied topically to the skin at a concentration sufficient to screen out effectively radiation from either the UV-A range or the UV-B range. The presence however, of a naturally-occurring substituted 1,3-diketone, which can provide broad spectrum protection both the UV-A and UV-B ranges, enables a lower than usual amount of synthetic organic sunscreen materials to be used to "top-up" the overall Sun Protection Factor of the composition to an exceptionally high level, without the risk of causing the type of skin damage or other health problems that can be associated with the use of higher levels of synthetic organic sunscreen materials alone.

In view of this, a relatively small amount of synthetic organic sunscreen optionally can be incorporated into the composition of the invention.

Examples of suitable synthetic organic sunscreens, when required, include those set out in Table 2 below, and mixtures thereof.

TABLE 2

| CTFA Name | Trade Name | Supplier |
|---|---|---|
| Benzophenone-1 | UVINUL 400 | BASF Chemical Co. |
| Benzophenone-2 | UVINUL D-50 | BASF Chemical Co. |
| Benzophenone-3 | UVINUL M-40 | BASF Chemical Co. |
| Benzophenone-4 | UVINUL MS-40 | BASF Chemical Co. |
| Benzophenone-6 | UVINUL D-49 | BASF Chemical Co. |
| Benzophenone-8 | SPECRA-SORB UV-24 | American Cyanamide |
| Benzophenone-10 | UVISTAT 2211 | Ward Blenkinsop |
| Benzophenone-12 | CYASORB UV531 | American Cyanamide |
| DEA Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Givaudin Corpn. |
| Octyl salicylate | SUNAROME WMO | Felton Worldwide |

TABLE 2-continued

| CTFA Name | Trade Name | Supplier |
| --- | --- | --- |
| PABA | PABA | National Starch |
| 2-Phenyl-benzimidazole-5-sulphonic acid | EUSOLEX 232 | EM Industries |
| TEA salicylate | SUNAROME W | Felton Worldwide |
| 3-(4-methylbenzy-lidene)-camphor | EUSOLEX 6300 | EM Industries |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The composition of the invention can accordingly optionally comprise from 0.1 to 10%, preferably from 1 to 5% by weight of an synthetic organic sunscreen material.

Optional Inorganic Sunscreens

The composition of the invention optionally can also comprise an inorganic sunscreen.

Examples of inorganic sunscreens include: titanium dioxide, having an average particle size of
<100 nm (also known as ultrafine titanium dioxide),
zinc oxide, having an average particle size of from 1 to 300 nm,
iron oxide, having an average particle size of from 1 to 300 nm,
silica, such as fumed silica, having an average particle size of from 1 to 100nm.

It should be noted that silica, when used as an ingredient in the composition according to the invention can provide protection from infra-red radiation.

Other Cosmetic Adjuncts

Examples of conventional adjuncts which can optionally be employed include preservatives, such as para-hydroxy benzoate esters; antioxidants, such butyl hydroxy toluene; humectants, such as glycerol, sorbitol, 2-pyrrolidone-5-carboxylate, dibutylphthalate, gelatin, polyethylene glycol, such as PEG 200-600; buffers, such as lactic acid together with a base such as triethanolamine or sodium hydroxide; waxes, such as beeswax, ozokerite wax, paraffin wax; plant extracts, in addition those containing a substituted 1,3-diketone, that can be derived from plant sources such as Aloe vera, cornflower, witch hazel, elderflower, cucumber; thickeners; activity enhancers; colourants; and perfumes. Cosmetic adjuncts can form the balance of the composition.

Use of the Composition

The composition according to the invention is intended primarily as a sun care product for topical application to human skin or hair, to provide protection from the harmful effects of excessive exposure to sunlight.

In use, a small quantity of the composition, for example from 1 to 5 ml, is applied to exposed areas of the skin or hair, from a suitable container or applicator and, if necessary, it is then spread over and/or rubbed into the skin or hair using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

Method for determination of Sun Protection Factor (SPF) in vitro

The method for the in vitro SPF determination of the composition of the invention involves the spectrophotometric scanning of stratum corneum between 400nm and 290nm utilising a Perkin Elmer Lamba 17 spectrophotometer equipped with a diffuse transmission detection system.

Guinea pig stratum corneum is used in place of human skin and the following procedure is followed.

i. Guinea pig stratum corneum is isolated as fine sheets from guinea pig skin and air dried.
  ii. A piece of the stratum corneum is applied to the outer surface of a 0.5 cm quartz cuvette using a drop of distilled water to seal the stratum corneum uniformly to the quartz surface.
  iii. The quarts cuvette carrying the piece of stratum corneum is placed in the light path of the spectrophotometer which for this purpose is fitted with a fluorescence cut-off filter. This filter eliminates the autofluorescence of the stratum corneum and filters out all transmissions above 400 nm.
  iv. The stratum corneum is scanned from 290 to 400 nm and the spectrum obtained is saved as the control.
  v. The cuvette with stratum corneum is removed from the spectrophotomete and the test material (i.e. sunscreen) is applied to the stratum corneum at the rate of 1.5 || l/cm$^2$, in accordance with German DIN protocol, and rubbed uniformly across the entire surface of the skin using ht finger fitted with a finger stall.
  vi. The applied sunscreen material is allowed to stand for 5 minutes at room temperature (20° C.) to enable it to dry, and then the sample is rescanned in the spectrophotometer as before from 290 to 400 nm. This spectrum is saved as the test spectrum. No spectral absorbance changes were observed with drying times between 2 to 15 minutes; the 5 minute drying time was therefore adopted as standard.
  vii. The control spectrum is subtracted form the test spectrum to provide the spectral absorbance of the test sample of sunscreen material and this absorbence is converted to transmission.
  viii. The in vitro Sun Protection Factor (SPF) is finally calculated form the transmission measurements as described by Diffey et al, in a paper entitled: "A new substrate to measure sunscreen protection factors throughout the ultra-violet spectrum" in J. Soc. Cosmet. Chem. 40, 127–133 (May/Jun. 1989); see especially page 130.

EXPERIMENT

The following experiment confirms the effectiveness as sunscreen agents of 2 naturally occurring substituted 1,3-diketones, as compared with 2 commercially available synthetic sunscreen agents.

In this experiment, albino guinea pigs are depilated on their backs. 24 hours later, a resin template containing three 2 cm × 2 cm apertures was strapped on the backs of the animals and the apertures marked. A solution of pongamol or curcumin at concentrations ranging from 0.25 to 2 mg/sq.cm. in alcohol was applied on the marked areas. A neighbouring patch was identically treated with alcohol alone. 15 minutes after application of the product, the template was strapped back on and the animal was irradiated by a Wotan Ultravitalux UV lamp (300 W) from a distance pf 15 cm for 6 mins. The template was removed and the erythema was scored 4 hours after irradiation and graded on a 5 point scale. For comparison, standard synthetic sunscreen agents, Parsol MCX and 1789 ex Givaudan were used. Curcumin and pongamol used in these studies were of natural origin and obtained from turmeric roots and karanja seed respectively.

| Compound | Erythema |
| --- | --- |
| Blank | 2.5–3.5 |
| Parsol MCX (0.3 mg/sq. cm) | 1.5–2.5 |
| Parsol 1789 (0.5 mg/sq. cm) | 1.0–1.5 |
| Curcumin (2.0 mg/sq. cm) | 0.0–1.0 |
| Pangamol (0.7 mg/sq. cm) | 0.5–1.0 |
| Pongamol (0.8 mg/sq. cm) | 0.0–1.5 |

It was concluded that both Curcumin and Pongamol were effective in terms of protection from erythema in guinea pigs.

EXAMPLES

The invention is further illustrated with reference to the following examples.

Example 1

This example illustrates a composition according to the invention comprising Pongamol as the natural substituted 1,3-diketone sunscreen agent. Results are also given showing the effectiveness of this composition using a panel of human volunteers.

Pongamol was incorporated at 1.2% by weight and 0.6% by weight in a vanishing cream base containing 18% by weight o stearic acid, 0.5% by weight potassium hydroxide, 1.0% by weight glycerine, 0.2% by weight preservative. A control cream did not contain pongamol. A rexin template containing three 1 cm × 1 cm apertures was strapped onto the arms of human volueners and the apertures marked out. The cream (5 mg/sq cm) was applied to the areas marked. 15 minutes later, the template was strapped back and irradiated for up to 6 minutes (depending on the skin colour of the volunteers) with a Wotan Ultravitalux UV lamp (300 W) from a distance of 15 cm. The template was removed and the tanning evaluated visually daily for 10 days. The results of evaluation at the end of 5 days are shown in Table 3 below:

TABLE 3

| Panellist | Conditions (duration of irradiation) | | Results (decreasing sunscreen efficacy, increasing tanning) |
| --- | --- | --- | --- |
| 1 | 5 minutes | Left arm | 1.2% > 0.6% > Control |
|   |           | Right arm | 1.2% > 0.6% > Control |
| 2 | 5 minutes | Left arm | 1.2% > 0.6% > Control |
| 3 | 5½ minutes | Left arm | 1.2% > 0.6% > Control |
| 4 | 5 minutes | Right arm | 1.2% > 0.6% > Control |

It was found that creams containing pongamol afforded protection from tanning in this experiment.

Example 2

This example illustrates the use of a natural substituted 1,3-diketone when incorporated together with a synthetic sunscreen in a vanishing cream base composition.

Pongamol was incorporated along with a known UV B sunscreen (Parsol MCX ex. Givaudan) in a vanishing cream base containing by weight 18% stearic acid, 0.5% potassium hydroxide, 1% glycerine, 0.2% preservative. The levels of Parsol MCX and Pongamol were 1.0 and 0.7; 1.5 and 0.4; 2.0 and 0.3; 2.5 and 0.3%. Creams containing Parsol MCX and Parsol 1789 (ex-Givaudan) in a vanishing cream base containing 18% stearic acid, 0.5% potassium hydroxide, 1.0% glycerine, 0.2% preservative were formulated. The levels of Parsol MCX and Parsol 1789 were 1.0 and 0.2; 1.0 and 0.5; 1.25 and 0.4; 2.5 and 0.2% respectively.

The forearm of each of a panel of volunteers was washed with soap and water and patted dry. A rexin template containing five 1 cm × 1 cm apertures was strapped onto the forearms of volunteers and the apertures marked out. The reflectance from the skin in the marked areas was determined using an instrument which quantified the reflectance from a circular patch of skin 1 cm in diameter. The various creams were applied (4 mg) onto the marked area. Fifteen minutes later, the template was strapped back on and the arms irradiated with a Wotan Ultravitalux UV lamp (300 W) from a distance of 15 cm. The templates were removed and the tanning evaluated visually (subjective score) on a 0 to 8 point scale and by measuring the reflectance. The results at the end of 5 days is given in the Table 4 below. All values are means of several independent determinations (numbers in parenthesis).

TABLE 4

| Parsol MCX: Parsol 1789 | Parsol MCX: Pongamol | Visual | Reflectance ($\alpha$ R) |
| --- | --- | --- | --- |
| Placebo |  | 3.30 ± 0.17 (14) | −208 ± 10 (10) |
| 1:0.2 |  | 1.35 ± 0.19 (14) | −119 ± 9 (10) |
| 1.25:0.4 |  | 0.93 ± 0.14 (14) | −75 ± 12 (10) |
| 2.5:0.2 |  | 0.68 ± 0.13 (14) | −69 ± 14 (10) |
|  | 1.0:0.7 | 1.21 ± 0.2 (7) | −23 ± 13 (5) |
|  | 1.5:0.4 | 0.77 ± 0.19 (6) | −30 ± 31 (6) |
|  | 2.0:0.3 | 0.83 ± 0.11 (6) | −36 ± 26 (6) |
|  | 2.5:0.3 | 0.68 ± 0.15 (7) | −14 ± 13 (5) |

From the above, it was concluded that Pongamol protects the skin from the effects of UV radiation in a manner analogous to a well-known UV-A sunscreen-Parsol 1789.

Example 3

This example illustrates a lotion according to the invention.

| Ingredient | % w/w |
| --- | --- |
| silicone surfactant | 10.0 |
| volatile siloxane | 14.0 |
| mineral oil | 1.5 |
| Pongamol | 1.5 |
| titanium dioxide (water-dispersible) | 2.5 |
| titanium dioxide (oil-dispersible) | 2.5 |
| 2-hydroxy octanoic acid | 1.0 |
| 2-hydroxy propanoic aCid | 5.0 |
| butylene glycol | 10.0 |

-continued

| Ingredient | % w/w |
|---|---|
| sodium chloride | 2.0 |
| l-proline | 0.1 |
| neutralising agent | qs |
| preservative | qs |
| perfume | qs |
| water | qs |

Example 4

This example illustrates a fluid cream according to the invention.

| Ingredient | % w/w |
|---|---|
| volatile siloxane (DC 345) | 8.2 |
| silicone surfactant (DC 3225C) | 12.0 |
| petroleum jelly | 0.5 |
| mineral oil | 1.5 |
| Pongamol | 2.0 |
| Parsol MCX (octyl methoxycinnamate) | 3.0 |
| titanium dioxide (oil-dispersible) | 2.0 |
| titanium dioxide (water-dispersible) | 2.0 |
| sodium chloride | 2.0 |
| butylene glycol | 10.0 |
| l-proline | 0.1 |
| 2-hydroxy octanoic acid | 1.0 |
| 2-hydroxy propanoic acid | 5.0 |
| neutralising agent | qs |
| preservative | qs |
| perfume | qs |
| water | qs |

Example 5

This example illustrates a cream according to the invention.

| Ingredient | % w/w |
|---|---|
| volatile siloxane (DC 345 Fluid) | 8.2 |
| silicone surfactant (DC 3225C) | 12.0 |
| mineral oil | 1.5 |
| Curcumin | 0.5 |
| petroleum jelly | 0.5 |
| Parsol MCX (octyl methoxycinnamate) | 1.5 |
| titanium dioxide (oil-dispersible) | 1.0 |
| titanium dioxide (water-dispersible) | 1.0 |
| 2-hydroxyoctanoic acid | 1.0 |
| 2-hydroxypropanoic acid | 5.0 |
| sodium chloride | 2.0 |
| butylene glycol | 10.0 |
| l-proline | 0.1 |
| neutralising agent (aqueous phase to 4.5) | q.s. |

-continued

| Ingredient | % w/w |
|---|---|
| preservative | q.s. |
| perfume | q.s. |
| water | to 100 |

Example 6

This example illustrates a lotion according to the invention

| Ingredient | % w/w |
|---|---|
| silicone surfactant (DC 3225C) | 10.0 |
| volatile siloxane (DC 345) | 14.0 |
| mineral oil | 1.5 |
| Pongamol | 0.5 |
| Curcumin | 0.5 |
| Parsol MCX | 3.0 |
| titanium dioxide (oil-dispersible) | 2.0 |
| titanium dioxide (water-dispersible) | 2.0 |
| butylene glycol | 10.0 |
| sodium chloride | 2.0 |
| l-proline | 0.1 |
| 2-hydroxy octanoic acid | 1.0 |
| 2-hydroxy propanoic acid | 5.0 |
| neutralising agent | qs |
| perfume | qs |
| preservative | qs |
| water | qs |

What is claimed is:

1. A sunscreen composition suitable for topical application to human skin or hair to provide protection from excessive exposure to ultra-violet rays, which comprises:

(i) an effective amount of a substituted 1,3-diketone which is 1,3-propanedione, 1-(4-methoxy-5-benzofuranyl)-3-phenyl having the structure:

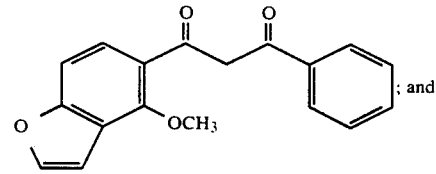

; and (ii) a physiologically acceptable vehicle for the substituted 1,3-diketone.

2. A composition according to claims 1, in which the 1,3-diketone forms from 0.01 to 15% by weight of the composition.

3. A composition according to claim 1, which is in the form of a cream or lotion.

* * * * *

UNITED STATES PATENT AND TRADEMARK OFFICE
CERTIFICATE OF CORRECTION

PATENT NO. : 5,152,983
DATED : October 6, 1992
INVENTOR(S) : Nambudiry et al.

It is certified that error appears in the above-indentified patent and that said Letters Patent is hereby corrected as shown below:

On title page, item [75]

"Visweswaria N. Collur" should read -- Collur V. Natraj --.

Signed and Sealed this

Twenty-sixth Day of July, 1994

Attest:

BRUCE LEHMAN

Attesting Officer     Commissioner of Patents and Trademarks